(12) United States Patent
Liniger et al.

(10) Patent No.: US 11,400,224 B2
(45) Date of Patent: Aug. 2, 2022

(54) SAFETY ARRANGEMENT AND MEDICAL DELIVERY DEVICE

(71) Applicant: SHL Medical AG, Zug (CH)

(72) Inventors: Jürg Liniger, Basel (CH); Martin Müri, Basel (CH); Thomas Thüer, Basel (CH); Declan Reilly, Basel (CH); Neil B. Cammish, Basel (CH); Stephan Olson, Danderyd (SE)

(73) Assignee: SHL MEDICAL AG, Zug (CH)

( * ) Notice: Subject to any disclaimer, the term of this patent is extended or adjusted under 35 U.S.C. 154(b) by 307 days.

(21) Appl. No.: 16/498,971

(22) PCT Filed: Mar. 28, 2018

(86) PCT No.: PCT/EP2018/057854
§ 371 (c)(1),
(2) Date: Sep. 27, 2019

(87) PCT Pub. No.: WO2018/178127
PCT Pub. Date: Oct. 4, 2018

(65) Prior Publication Data
US 2021/0085884 A1    Mar. 25, 2021

(30) Foreign Application Priority Data

Mar. 29, 2017  (EP) .................................. 17163522

(51) Int. Cl.
*A61M 5/315* (2006.01)
*A61M 5/24* (2006.01)
*A61M 5/32* (2006.01)

(52) U.S. Cl.
CPC .......... *A61M 5/31501* (2013.01); *A61M 5/24* (2013.01); *A61M 5/3202* (2013.01); *A61M 2205/02* (2013.01)

(58) Field of Classification Search
CPC .. A61M 5/31501; A61M 5/24; A61M 5/3202; A61M 2205/02
See application file for complete search history.

(56) References Cited

U.S. PATENT DOCUMENTS 8,715,246 B2    5/2014  Giambattista et al.
2012/0143143 A1  6/2012  Giambattista et al.
(Continued)

FOREIGN PATENT DOCUMENTS

CN    101454035 A    6/2009
EP     2201975 A1    6/2010
(Continued)

*Primary Examiner* — Dung T Ulsh
(74) *Attorney, Agent, or Firm* — McDonnell Boehner Hulbert & Berghoff LLP

(57) ABSTRACT

A safety arrangement for being used in a medicament delivery device, comprising a container holder with a body section and a flange seat and a shell. The container holder is arranged to receive a container with a longitudinal body at one end passing over into a distal flange and at an opposite end passing over into a proximal orifice via a shoulder, such that the distal flanges of the container contacts the flange seat of the container holder. Moreover, the container holder is arranged in the shell such that the container holder is movable in a proximal direction in relation to the shell. A blocking element is arranged between the shell and the container holder. A blocking initiating structure is arranged to reposition the blocking element when the container holder is moved in the proximal direction in relation to the shell from a first position to a second position.

15 Claims, 4 Drawing Sheets

(56) References Cited

U.S. PATENT DOCUMENTS

2012/0259288 A1 10/2012 Wagner et al.
2015/0126938 A1* 5/2015 Vogt ................... A61M 5/3202
    604/192
2017/0007767 A1* 1/2017 Schabbach .............. B29C 45/14

FOREIGN PATENT DOCUMENTS

EP         3138595 A1  3/2017
WO      2007138317 A1  12/2007

* cited by examiner

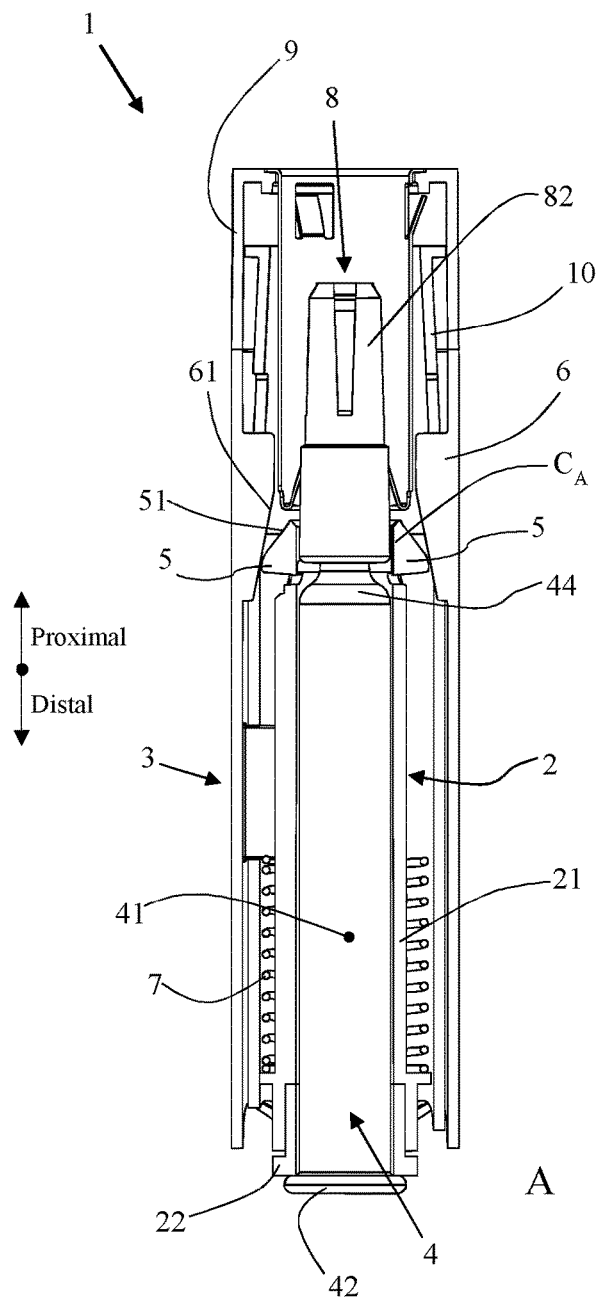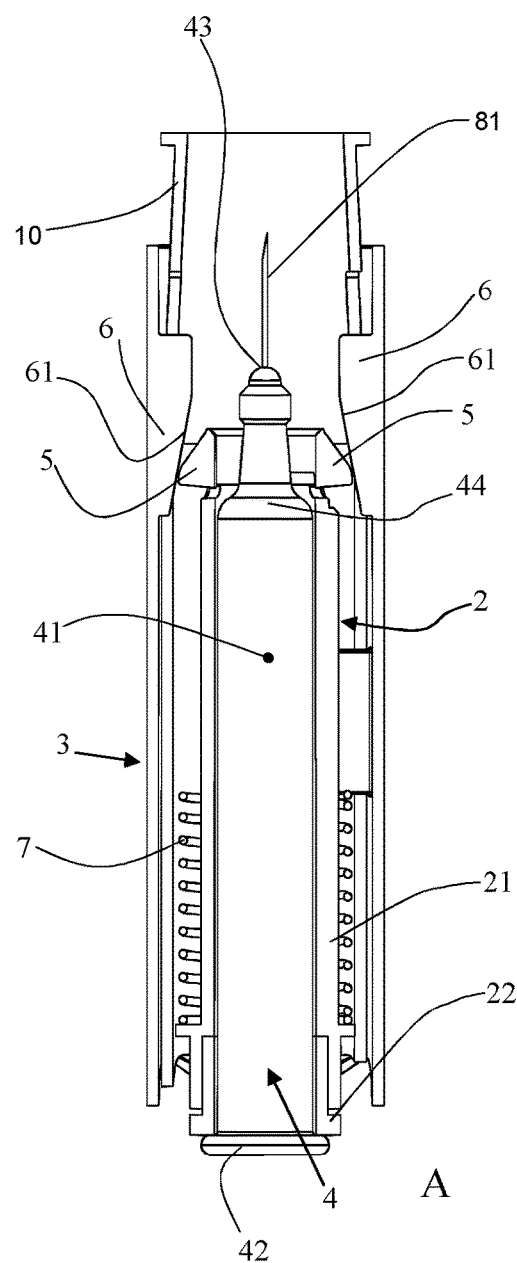
Fig. 1
Fig. 2

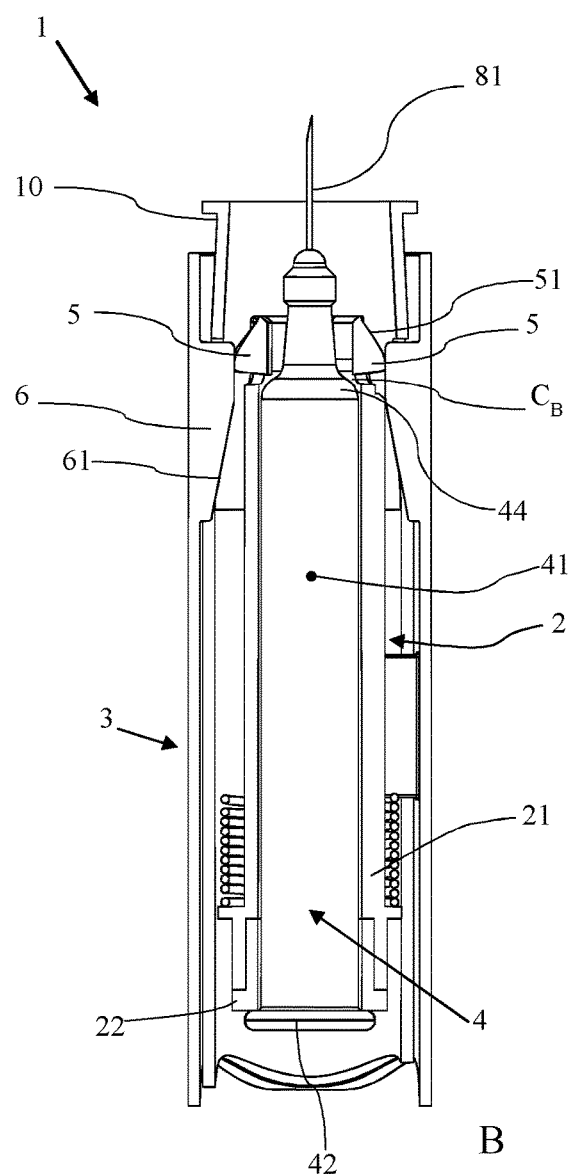
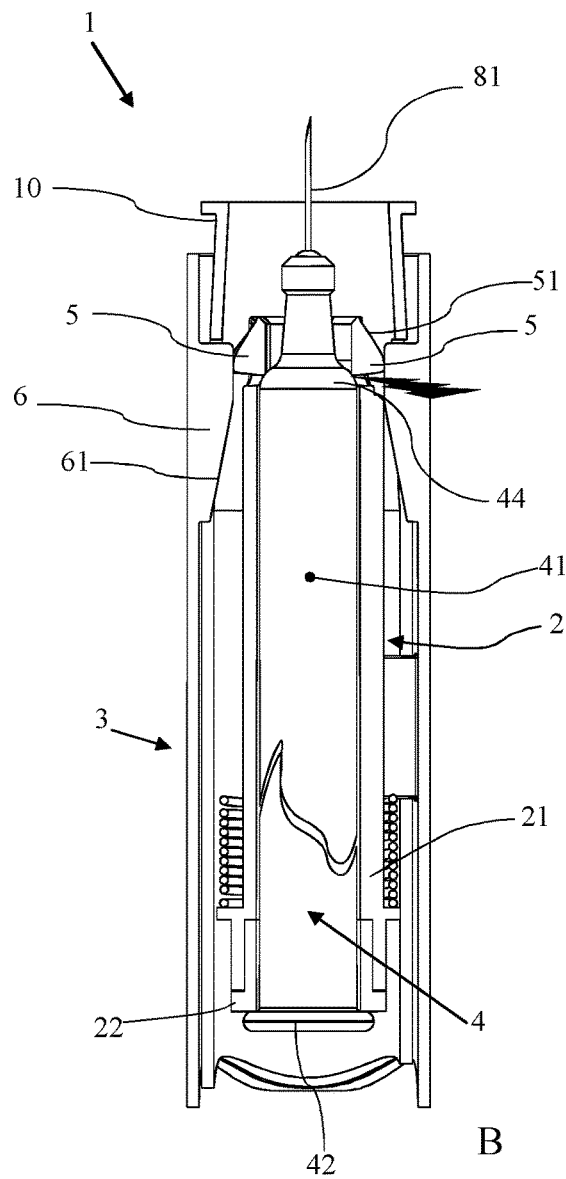
Fig. 3
Fig. 4

SAFETY ARRANGEMENT AND MEDICAL DELIVERY DEVICE

CROSS REFERENCE TO RELATED APPLICATIONS

The present application is a U.S. National Phase Application pursuant to 35 U.S.C. § 371 of International Application No. PCT/EP2018/057854 filed Mar. 28, 2018, which claims priority to European Patent Application No. 17163522.0 filed Mar. 29, 2017. The entire disclosure contents of these applications are hereby incorporated by reference into the present application.

TECHNICAL FIELD

The present invention relates to a safety arrangement to be used in a medicament delivery device according to the preamble of independent claim 1 and more particularly to a safety arrangement comprising a container holder arranged to receive a flange-retained syringe, cartridge or similar containers for delivery of a medicament via a needle.

The present invention also relates to a medicament delivery device especially modified to comprise and cooperate with such a safety arrangement.

Such a safety arrangement device can be implemented in medicament delivery systems, both manually operated and automatic, for administering therapeutic agents in the body of human or animal patients. The present invention is especially advantageous when applied to automatic injection devices, housing a container filled with a therapeutic agent, which, when operated, causes the container to move in a proximal direction towards a delivery site of the patient and a needle on the container to project out of the device housing to inject the therapeutic agent into a patient's body.

This automatism is typically achieved by a mechanism, which, when triggered by an operator, automatically executes the delivery of the therapeutic agent to the patient. Preferably, but not exclusively, the present invention can be incorporated in injection devices intended for self-administration by patients, or for administration by untrained personnel, also known as auto-injection devices. These devices are expressly designed to overcome manipulation and safety difficulties associated with administration of a drug through a needle-based delivery device by unskilled operators.

BACKGROUND ART

In needle-based medicament delivery devices often a medicament container with a medicament is placed in a container holder which is movably arranged in a shell. In some embodiments the medicament container has a flange at a distal end. In such embodiments the medicament container is typically held by container holder at its flange. Furthermore, the medicament container can be provided with an injection needle. Thereby, it is paramount to prevent damage of the injection needle, such as deformation, and to avoid its accidental contact with contaminating objects or environment until use. Therefore, in order to preserve the mechanical functionality of the needle and its sterility, it is a common practice to provide a needle arrangement of such delivery devices with needle covers, also called needle shields.

In particular, needle arrangements comprising a so-called rigid needle shield (RNS) which typically include a rigid outer component (e.g. molded in plastic material such as polypropylene), adapted for enabling easier handling and removal of the overall shield, in combination with a relatively flexible, softer inner component (e.g. made of an elastomer such as rubber) having good sealing properties are widespread. The outer component and the inner component of the shields are interconnected, so as to allow removal of the overall shield by an operator, for instance integrally with an external cap.

Particularly in the context of medicament delivery device adapted for injection of small quantities of therapeutic agent, in the order of 1 millilitre or similar, the configuration is such that the abovementioned RNS generally have a diameter which is essentially the same as, or larger than, the diameter of a barrel of the medicament container. Owing to this, the containers are often exclusively held at their distal flanges to be held in the delivery devices and prevent their exit from a proximal opening of the delivery devices.

Even when provided with a distal flange, however, medicament containers such as syringes, cartridges and similar remain prone to breakages, for several reasons e.g. during an injection procedure, due to the pressure applied by a plunger rod activated by a driving mechanism of the medicament delivery device; and/or because of tissue resistance during needle penetration and/or in case the medicament delivering devices wherein they are lodged are dropped and/or pre-existing micro cracks in the medicament container as is common. Containers are often generally made of glass, which is favourable mainly because it offers stability, easy sterilization and an inert environment ensuring no reaction with the loaded therapeutic agent. In case of breakage, especially in consideration of the above introduced rigid needle shield configuration, elements of broken medicament container cannot be effectively held at the front of the delivery device and, due to the force applied by the driving mechanism for displacing the plunger rod, tend to be ejected from the delivery device. In particular, ejecting the proximal portion of the medicament container carrying the injection needle can be dangerous.

In this context, several solutions have been proposed for fail-safe systems for medicament delivery devices which deal with the unfortunate occurrence of medicament container or syringe breakage.

In U.S. Pat. No. 8,715,246 B2, there is disclosed a holder arrangement wherein holders, in the form of flexible arms, substantially and constantly hold the proximal shoulder portion of a medicament container, that is even when the container is intact. Thus, parts of the container are prevented from moving further in a proximal direction in case of container breakage. The holders are especially conceived to come in contact with a needle shield and to let it slide through, allowing its passage.

However, the arrangement proposed in U.S. Pat. No. 8,715,246 B2 is affected by a number of drawbacks. Flexible arms permanently gripping on a syringe shoulder and integrating protrusions which come to rest in a gap between a rigid needle shield and such shoulder bring about the problem of making the removal of the rigid needle shield by an operator more difficult. In fact, such kind of holder may irregularly increase the resistance to removal of the needle shield and make the operation more unpredictable. Not only that, but a design wherein the needle shield needs to come into contact with flexible arms of the holder arrangement in normal operative conditions (for instance, when a medicament container is loaded in a container holder from a distal end of the delivery device and whenever the needle shield is inserted or removed) is critical to the integrity, both structural and in terms of sterility, of the medicament container and attached needle. The inevitable, designed-in interference between flexible arms of holders and the rigid needle shield may damage the needle or partially expose it to a different environment, already at a non-injecting stage.

Moreover, a design incorporating thin, elongated flexible arms and ledges is liable to damage and unnecessarily complicates manufacturing and assembling processes.

Therefore, there is a need for a solid safety arrangement for a medicament delivery device which effectively and reliably prevents pieces of a broken container lodged in the delivery device from hazardously falling out or being ejected from a proximal opening of the device. At the same time, there is a need for such a safety system to enact its fail-safe function just when it is required, therefore minimally interfering with the ordinary operation of the delivery device. There is also a concurrent need to overcome risks of compromising the integrity of a drug container of the delivery device by activation of the safety arrangement, which can occur by disturbing a needle shield. A safety arrangement for a medicament delivery device should also not imply an excessive complication of the overall design of the delivery device.

Disclosure of the Invention

According to the invention this need is settled by a safety arrangement as it is defined by the features of independent claim 1, and by a medicament delivery device as it is defined by independent claim 7. Preferred embodiments are subject of the dependent claims.

In particular, the invention deals with a safety arrangement, intended for use in a medicament delivery device, which comprises a container holder with a body section and a flange seat. A shell of the safety arrangement at least partially encloses the container holder, acting as a housing. The container holder is arranged to receive a container, such as a syringe or a cartridge or similar, which is preferably pre-filled with a therapeutic agent or medicament. The container comprises a longitudinal body, typically a barrel taking the form of a cylindrical tube, which at one end passes over into a distal flange and at an opposite end passes over into a proximal orifice via a shoulder. A needle can be mounted on or staked within the orifice of the container, for delivery of the therapeutic agent or medicament. In order to protect the needle, a medicament delivery device integrating a safety arrangement according to the present invention preferably comprises a needle arrangement comprising a needle cover which is removably mounted on the needle and needle hub, by way of example a rigid needle shield as described above. A diameter of the needle cover may be at least substantially the same as, or larger than, a diameter of the longitudinal body of the container. In this connection substantially the same can include that there is a variation in the diameters which is not meaningful such as, e.g., in a range of about 0.1 mm or less, or in a range of 0.2 mm or less. The medicament delivery device may comprise a cap which engages or grips the needle arrangement so that removal of the cap from the device also achieves removal of the rigid needle shield to uncover the needle. The safety arrangement of the present invention can be itself a needle safety device (also referred to as NSD) or it can be part of such a needle safety device or autoinjector.

The configuration of the safety arrangement is such that the container holder is arranged to receive the container such that the distal flange of the container contacts the flange seat of the container holder. The container holder is arranged in the shell such that the container holder is movable in a proximal direction in relation to the shell.

In the context of the present invention, the term "proximal" is used to refer to a portion, an extremity or a component of a safety arrangement—and, analogously, of a medicament delivery device incorporating such a safety arrangement—which is located closest to a medicament delivery site, when the safety arrangement is in use in connection with administering of such medicament to a patient.

Conversely, the term "distal" is used to refer to a portion, an extremity or a component of a safety arrangement—and, analogously, of a medicament delivery device incorporating such a safety arrangement—which is located furthest away from a medicament delivery site, when the safety arrangement is in use in connection with administering of such medicament to a patient.

Preferably, the longitudinal body of the container, the body section of the container holder and the shell around the container holder are coaxial. In this configuration, the container holder is movable, relative to the shell, along a common axis.

The drawbacks affecting the prior art are overcome by providing the safety arrangement with a blocking element and with a corresponding blocking initiating structure. The blocking element is arranged between the shell and the container holder. The blocking initiating structure is arranged to repositioning the blocking element when the container holder moves in the proximal direction relative to the shell, e.g., upon initiation of an injection process which can automatically be triggered by a driving mechanism of a medicament delivery device, to prevent at least a portion of the container from leaving the shell when breaking. By virtue of the blocking element and the blocking initiating structure, the container or at least broken portions thereof and particularly portions with the orifice potentially carrying the needle can be prevented from passing the blocking element. Like this, the container or the mentioned portions can be hindered from leaving the shell such that they can be held inside the system. In that way, particularly potentially harmful parts such as a part carrying the needle or parts contaminated with a substance such as a medicament or pathogens can be kept safe inside the system. Thus, the safety of the medical delivery device into which the safety arrangement is integrated can be increased.

The forward movement of the container holder relative to the shell in the proximal direction can function to bring the needle to a position suitable for the execution of an injection and for subsequent medicament delivery. Such movement can be operatively connected to the activation of a driving mechanism of a medicament delivery device equipped with the safety arrangement according to the present invention. Preferably, a driving mechanism of the medicament delivery device is arranged to forward a plunger rod into the body of the container when activated, exercising a corresponding pressure within the container and on the medicament therein stored. The medicament is thus injected to a body via the needle mounted on the proximal orifice of the container. The driving mechanism can be embodied for manual or semi-automatic and particularly for automatic forwarding of the plunger rod.

By the abovementioned movement, the holder is brought from a first position to a second position. The first position can correspond to an inactive status, wherein the safety arrangement, or better the associated delivery device, is in a non-injecting configuration preferably covered by the shell. Such first position can, for instance, correspond to an extended state of a spring element which is arranged between the container holder and the shell. The force exerted by the spring pushes the container holder and the shell towards the first position, or more generally keeps them in such first position. On the other hand, the second position can correspond to an active or delivery status, wherein the safety arrangement, or the associated delivery device, is in an injecting configuration. When the container holder is in the second position in relation to the shell, the needle cover has preferably already been removed and the needle can be exposed to pierce the skin of a patient. In such second state, the spring element can be in a partially compressed state.

Advantageously, thanks to the special conception of the present inventive solution, the repositioning by the blocking initiating structure of the blocking element prevents the container and particularly the shoulder thereof from passing the blocking element in the proximal direction, in a way that:

no interference of the holder or of the blocking element is created with the needle arrangement, such as a rigid needle shield, therefore preventing any adverse contact with the needle protection which may affect the integrity of the needle;

no disturbance to a smooth extraction of the needle arrangement by an operator is caused;

no complicated components are incorporated in the safety arrangement; and particularly, when the container breaks, the container or broken portions thereof are prevented from leaving the shell such that the safety of the device can be essentially increased.

In a possible embodiment of the present invention, the blocking element is integral with the shell. Accordingly, the blocking initiating structure is made integral with the container holder, or with another part of the safety arrangement which moves relatively to the shell.

Preferably, the blocking element is integral with the container holder. In this case, the blocking initiating structure preferably is integral with the shell or with another component of the safety arrangement which moves relatively to the container holder. The term "being integral" in this connection can relate to a one-piece construction or to a fixed assembly of the various part or components.

The blocking initiating structure or the blocking element preferably comprises a ramp along which the blocking element or the blocking initiating structure, respectively, travels when the container holder is moved in relation to the shell from the first position to the second position. In other words, one of the blocking initiating structure and the blocking element preferably comprises a ramp along which the other one of the blocking element and the blocking initiating structure travels when the container holder is moved in relation to the shell from the first position to the second position. In this case, the blocking element or the blocking initiating structure can preferably comprise a counter-ramp contacting the ramp of the blocking initiating structure or the blocking element, respectively, when the container holder is moved in relation to the shell from the first position to the second position. Thus, blocking element and blocking initiating structure cooperate to achieve a repositioning of the blocking element which, when the container holder and the shell are in the second position, excludes any possibility that the shoulder of the container may go past the blocking element in the proximal direction. The blocking element repositioning can happen by way of a movement of the blocking element radially towards a common central axis of the longitudinal body of the container, of the body section of the container holder and of the shell or, more generally, towards the needle.

A further aspect of the present invention deals with a medicament delivery device incorporating a safety arrangement as described and further comprising a needle arrangement as well as a container as above introduced. The container used in such delivery device may be a syringe, for instance made of glass.

In particular, a medicament delivery device comprises a container, a needle arrangement, a container holder, a shell, a blocking element and a blocking initiating structure. The container has a longitudinal body, a distal flange, a shoulder and a proximal orifice. The longitudinal body at one end passes over into the distal flange and at an opposite end passes over into the orifice via the shoulder. The needle arrangement has a needle mounted to the orifice of the container. The container holder has a body section and a flange seat. The container is arranged in the body section of the container holder such that the distal flange of the container contacts the flange seat of the container holder. The container holder is arranged in the shell such that the container holder is movable in a proximal direction in relation to the shell. The blocking element is arranged between the shell and the needle arrangement. The blocking initiating structure is arranged to reposition the blocking element towards the needle of the needle arrangement when the container holder is moved in the proximal direction in relation to the shell from a first position to a second position to prevent the container or at least a portion thereof from leaving the shell when breaking.

The medicament delivery device according to the present invention may include a needle sleeve configured to be projectable, to cover the needle or generally the needle arrangement; and retractable, to expose the needle, depending on the situation. Such a needle sleeve is particularly designed to prevent, after injection, an accidental contact of the protruding needle by any person. Hence, the needle sleeve enables a so-called "safe mode". The projection or retraction of the needle sleeve is preferably activated by a dedicated driving mechanism which can cooperate with the safety arrangement of the present invention but is preferably not part thereof. Moreover, the driving mechanism of the needle sleeve is preferably not coupled with the motion of the container, i.e. it is independent from the driving mechanism arranged to forward a plunger rod into the body of the container.

Advantageously, in a medicament delivery device according to the preset invention a clearance is preferably provided between the blocking element and the needle arrangement when the container holder is in the first position in relation to the shell.

Also, a further clearance can be advantageously provided between the blocking element and the shoulder of the container when the container holder is in the second position in relation to the shell, with the blocking element already displaced to obstruct any potential passage of the container, and the container is undamaged.

Conversely, when the blocking element is displaced to obstruct the passage of the container but the container is damaged, it is envisaged that the blocking element comes to contact with the container's shoulder; to best avoid any ejection of container fragments.

In a possible embodiment of the medicament delivery device according to the present invention, the blocking element contacts the shoulder of the container only when the container is damaged, whether with the container holder in the second position in relation to the shell or after injection, when the safe mode is activated.

In one embodiment, the blocking element is integral with the shell. However, the blocking element preferably is integral with the container holder.

Preferably, the needle arrangement comprises a needle cover removably mounted to the needle such that the needle is protected. Thereby, a diameter of the needle cover preferably is at least substantially the same as a diameter of the body of the container.

Preferably, the blocking element, after being repositioned by the blocking initiating structure, is arranged to prevent the shoulder of the container from passing the blocking element in the proximal direction. Like this, the container or portions thereof can be held back in the device such that they cannot escape or shoot out of the device.

Preferably, a clearance is provided between the blocking element and the needle arrangement when the container holder is in the first position in relation to the shell. Like this, the needle arrangement can conveniently be handled without any obstruction by the blocking element.

Preferably, a clearance is provided between the blocking element and the shoulder of the container when the container holder is in the second position in relation to the shell and the container is undamaged. This can further improve an unhindered handling of the needle arrangement in use.

Preferably, the blocking element contacts the shoulder of the container only when the container is damaged. Like this, it can be achieved that besides a situation of an accident the blocking element does not influence any other parts of the device and particularly not the container or the needle arrangement.

Preferably, the body of the container is made of glass. Such glass body may be advantageous in terms of sterility and the like.

Preferably, the container is a syringe. Such container may allow for an efficient arrangement of a device according to the invention.

Preferably, the medicament delivery device comprises a driving mechanism arranged to forward a plunger rod into the body of the container when being activated. Thereby, the driving mechanism can be embodied for manual or semi-automatic and particularly for automatic forwarding or displacing of the plunger rod. Such driving arrangement allows for a particularly convenient delivery or injection of the medicament.

Preferably, the blocking initiating structure or the blocking element comprises a ramp along which the blocking element or the blocking initiating structure, respectively, travels when the container holder is moved in relation to the shell from the first position to the second position. In other words, one of the blocking initiating structure and the blocking element preferably comprises a ramp along which the other one of the blocking element and the blocking initiating structure travels when the container holder is moved in relation to the shell from the first position to the second position.

Further, the blocking element or the blocking initiating structure preferably comprises a counter-ramp contacting the ramp of the blocking initiating structure or the blocking element, respectively, when the container holder is moved in relation to the shell from the first position to the second position. In other words, one of the blocking element and the blocking initiating structure preferably comprises a counter-ramp contacting the ramp of the other one of the blocking initiating structure and the blocking element, when the container holder is moved in relation to the shell from the first position to the second position.

BRIEF DESCRIPTION OF THE DRAWINGS

The safety arrangement according to the invention as well as medicament delivery device according to the invention are described in more detail hereinbelow by way of an exemplary embodiment and with reference to the attached drawings, in which:

FIG. 1 shows a partial cross sectional side view of an embodiment of a medicament delivery device according to the invention provided with an embodiment of a safety arrangement according to the invention, wherein a container holder and a shell are in a first position corresponding to a non-injecting configuration;

FIG. 2 shows a partial cross sectional side view of the medicament delivery device of FIG. 1, wherein a cap and a rigid needle shield of a needle arrangement are removed;

FIG. 3 shows a partial cross sectional side view the medicament delivery device of FIG. 1, wherein the container holder and the shell are in a second position corresponding to an injecting configuration;

FIG. 4 shows a partial cross sectional perspective view of the medicament delivery device in the second position of FIG. 3, wherein a container lodged in the holder is broken;

DESCRTIPTION OF EMBODIMENTS

Figure 5:
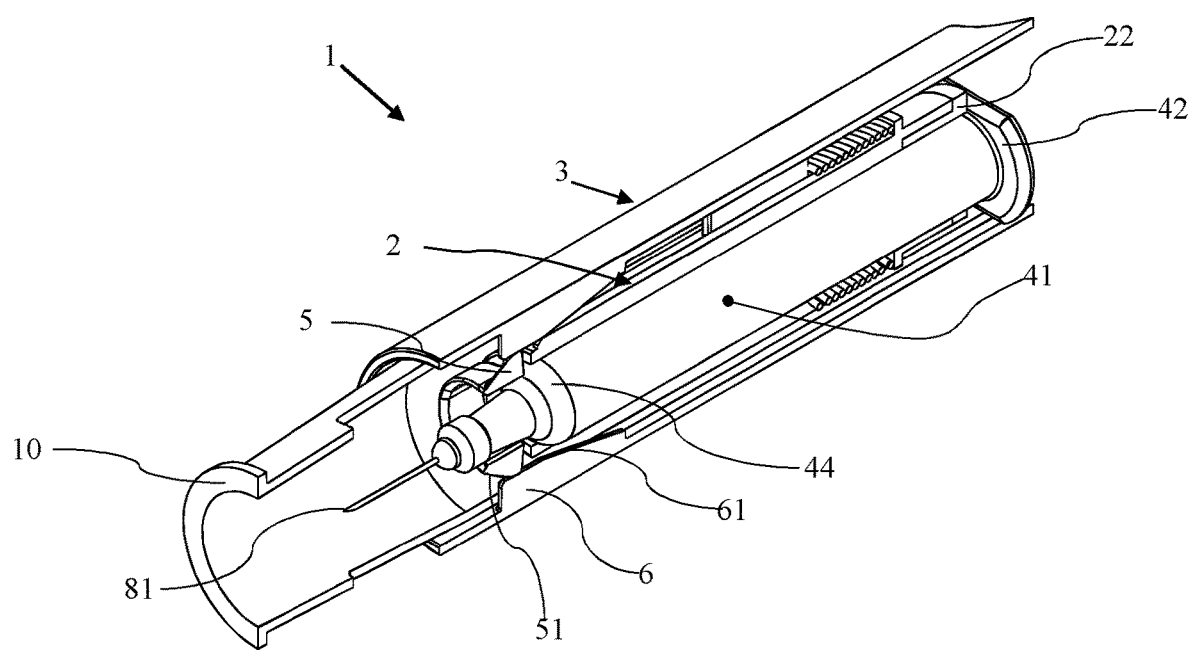
FIG. 5 shows a partial cross sectional view of the medicament delivery device of FIG. 3, after an injection has been carried out and a safe mode has been activated through projection of a needle sleeve to avoid accidental contact of an operator with the needle.

In the following description, certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

With reference to FIG. 1, a medicament delivery device 1 provided with a safety arrangement according to the present invention is shown. The safety arrangement comprises a container holder 2 with a body section 21 and a flange seat 22; and a shell 3. The container holder 2 receives a container 4 with a longitudinal body 41 at one end passing over into a distal flange 42. In the present case, the container takes the form of a glass syringe 4. At an opposite end, the container's longitudinal body 41 passes over into a proximal orifice 43 (not visible in FIG. 1) via shoulder 44. The distal flange 42 of the container 4 contacts the flange seat 22 of the container holder 2. In FIG. 1, the container holder 2, which is coaxially arranged in the shell 3 in a way that it is movable in a proximal direction in relation thereto, is in a first position A corresponding to a non-injecting configuration or an initial inactive status. A spring element 7 arranged between the container holder 2 and the shell 3 forms part of an activation or driving mechanism of the medical delivery device 1. In FIG. 1, a cap 9 is still mounted to guard a needle arrangement 8. The needle arrangement 8 comprises a needle cover 82, alternatively referred to as rigid needle shield (RNS), mounted to a needle 81 (not visible in FIG. 1) such that the needle 81 is protected. As it can be appreciated from FIG. 1, the needle cover 82 has, at least at a distal end thereof, the same diameter as the longitudinal body 41 of the container 4.

A blocking element 5, which takes in the embodiment shown the form of flexible security teeth, is arranged between the shell 3 and the container holder 2. Relatively to the embodiment of FIG. 1, the blocking element 5 is made integral with the container holder 2.

A blocking initiating structure 6 is arranged to reposition the blocking element 5 when the container 4 is moved in the proximal direction. In the embodiment represented, the blocking initiating structure 6 is made integral with the shell 3 and comprises a ramp 61 along which the blocking element 5 travels when the container holder 2 and the shell 3 are moved in relation to each other. In order to allow smooth movement and create a well aligned pathway, the blocking element 5 comprises a counter-ramp 51 contacting the ramp 61 when the container holder 2 and the shell 3 are moved in relation to each other.

In the first position A shown in FIG. 1 and FIG. 2, a clearance $C_A$ is provided between the blocking element 5 and the needle arrangement 8, namely the needle cover 82. Thus, when the needle cover 82 is removed by an operator, for instance by uncapping the delivery device 1, no undue disturbing resistance is encountered and integrity of the needle 81 is ensured. In FIG. 2 it is shown the medicament delivery device 1 when the cap 9 has been removed. The cap 9 is in this case provided with clamping means which fasten the needle cover 82 in such a way that a concurrent removal of the cover together with the cap 9 is enabled.

When, for instance, a driving mechanism (not shown in the FIGS.) of the delivery device 1 is activated to forward a plunger rod into the body 41 of the container 4, the ensuing pressure on the container 4 also determines a movement of the container holder 2 in the proximal direction in relation to the shell 3. Eventually, the container holder 2 comes to take a second position B, which is represented in FIGS. 3 and 4. Accordingly, the blocking element 5 travels along the ramp 61 and is repositioned towards the needle 81 of the needle arrangement 8, thus being arranged to obstruct the passage of the container 4 in the proximal direction. In fact, in this configuration the shoulder 44 of the container 4 is prevented from passing the blocking element 5 in the proximal direction.

A clearance $C_B$ is provided between the blocking element 5 and the shoulder 44 of the container 4, when the container holder 2 is in the second position B in relation to the shell 3 and the container 4 is undamaged, as shown in FIG. 3.

Figure 6:
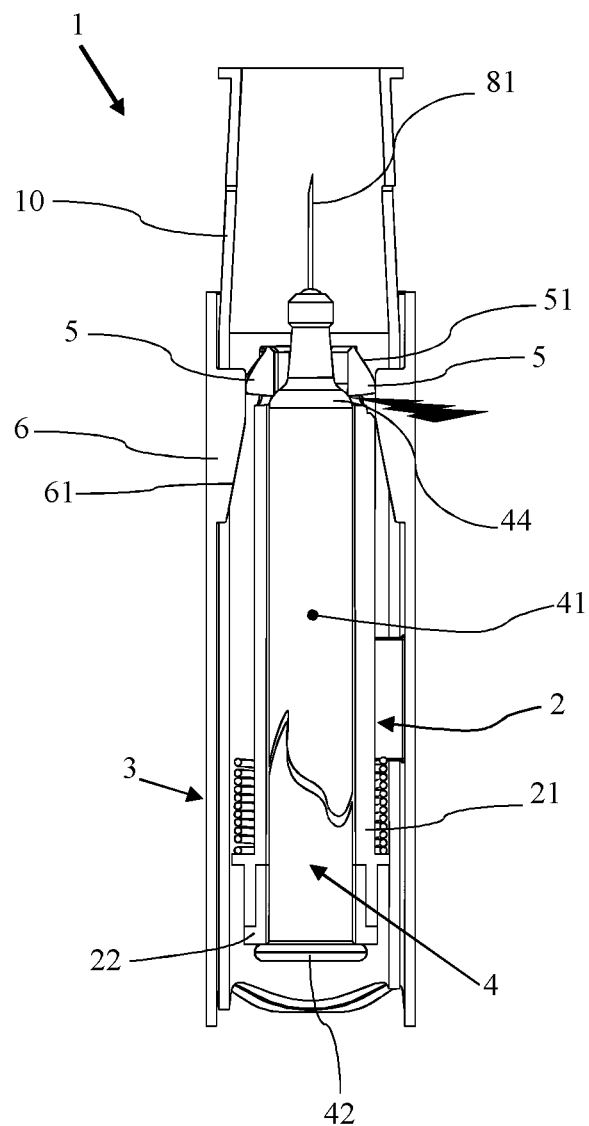
FIG. 6 shows a partial cross sectional view of the medicament delivery device of FIG. 4, after an injection has been at least partially carried out or attempted and a safe mode has been activated through projection of a needle sleeve to avoid accidental contact of an operator with the needle.

When, instead, the container 4 is damaged, as in the case illustrated in FIGS. 4 and 6, owing to the tendency of broken fragments or portions of the container 4 to shoot out, the blocking element 5 comes to abut against the shoulder 44 of the container 4. The safety arrangement according to the present invention can be adjusted to allow contact between the blocking element 5 and the shoulder 44 only when the container 4 is damaged.

The medicament delivery device 1 further comprises a needle sleeve 10 configured to be projectable for covering the needle 81 (or, generally, the needle arrangement 8, as can be seen in FIG. 1) and retractable for exposing the needle 81. As already mentioned, the needle sleeve 10 is especially aimed at preventing, after injection, an accidental contact of an operator with the protruding needle 81. This function, which can be called "safe mode", is exemplified in FIGS. 5 and 6, where the needle sleeve 10 is outstretched to laterally wrap the needle 81 and to create a spacing between the needle tip and a proximal extremity of the sleeve large enough that no accidental contact with a delivery device operator can happen. In the configurations of FIGS. 5 and 6, the injection has been either fully carried out or partially executed or attempted; the container holder 2 has reached its second position B with respect to the shell 3; and the blocking element 5 has already been repositioned to prevent a potential passage of the container 4 or of bits thereof in the proximal direction. In FIG. 5, an undamaged container 4 is represented; whereas in FIG. 6 the container 4 is broken and the blocking element 5 abuts against the shoulder 44 of the container 4. The projection or retraction of the needle sleeve 10 is preferably activated by a dedicated driving mechanism (not shown). Incidentally, in the non-injection configuration of FIGS. 1 and 2, the needle sleeve 10 is represented only partially stretched out. In the injection configuration of FIGS. 3 and 4, instead, the needle sleeve 10 is retracted to expose the needle 81 so that an injection can be executed.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A safety arrangement for being used in a medicament delivery device, comprising
   a container holder having a proximal end portion, a body section and a flange seat;
   a shell comprising an inner surface; and
   a blocking initiating structure positioned on the inner surface, where the blocking initiating structure comprises a dimensionally fixed ramp having a distal end and a proximal end, where the proximal end of the ramp projects radially inward a greater distance than the distal end of the ramp, wherein
   the container holder is arranged to receive a container with a longitudinal body at one end passing over into a distal flange and at an opposite end passing over into a proximal orifice via a shoulder such that the distal flange of the container contacts the flange seat of the container holder, and
   the container holder comprises a blocking element located at the proximal end portion, where the blocking element has a first clearance relative to the shoulder large enough to accept a distal end of a needle cover when engaged with the shoulder, and where proximal movement of the container holder relative to the shell after removal of the needle cover causes the blocking element to move to a second clearance such that the blocking element abuts the shoulder,
   wherein the blocking element engages and slides along the ramp during the proximal movement of the container holder from a first position to a second position such that the blocking element moves radially inward from the first clearance to the second clearance to prevent at least a portion of the container from leaving the shell when broken.

2. A safety arrangement according to claim 1, wherein the blocking element is integral with the container holder.

3. A safety arrangement according to claim 1, wherein the blocking initiating structure is integral with the shell.

4. A safety arrangement according to claim 1, wherein the blocking element comprises a counter ramp that engages the ramp when the container holder is moved in relation to the shell from the first position to the second position.

5. A medicament delivery device comprising
   a container with a longitudinal body, a distal flange, a shoulder and a proximal orifice, wherein the longitudinal body at one end passes over into the distal flange and at an opposite end passes over into the orifice via the shoulder;
   a needle arrangement with a needle mounted to the orifice of the container;
   a container holder having a proximal end portion, a body section and a flange seat;
   a shell comprising an inner surface; and
   a blocking initiating structure positioned on the inner surface, where the blocking initiating structure comprises a dimensionally fixed ramp having a distal end and a proximal end, where the proximal end projects radially inward a greater distance than the distal end of the ramp, wherein
   the container is arranged in the body section of the container holder such that the distal flange of the container contacts the flange seat of the container holder, and
   the container holder comprises a blocking element located at the proximal end portion, where the blocking element has a first clearance relative to the shoulder large enough to accept a distal end of a needle cover when engaged with the shoulder, and where proximal movement of the container holder relative to the shell after removal of the needle cover causes the blocking element to move to a second clearance such that the blocking element abuts the shoulder,
   wherein the blocking element engages and slides along the ramp during the proximal movement of the container holder from a first position to a second position such that the blocking element moves radially inward from the first clearance to the second clearance to prevent at least a portion of the container from leaving the shell when broken.

6. A medicament delivery device according to claim 5, wherein the blocking element is integral with the container holder.

7. A medicament delivery device according to claim 5, wherein the needle cover is removably mounted to the needle and the shoulder such that the needle is protected.

8. A medicament delivery device according to claim 7, wherein a diameter of the needle cover is at least substantially the same as a diameter of the body of the container.

9. A medicament delivery device according to claim 5, wherein the blocking element, after being repositioned by the blocking initiating structure, is arranged to prevent the shoulder of the container from passing the blocking element in the proximal direction.

10. A medicament delivery device according to claim 5, wherein the second clearance occurs when the container holder is in the second position in relation to the shell and the container is undamaged.

11. A medicament delivery device according to claim 5, wherein the blocking element directly contacts the shoulder of the container only when the container is damaged.

12. A medicament delivery device according to claim 5, wherein the body of the container is made of glass.

13. A medicament delivery device according to claim 5, wherein the container is a syringe.

14. A medicament delivery device according to claim 5, comprising a driving mechanism arranged to forward a plunger rod into the body of the container when being activated.

15. A medicament delivery device according to claim 5, wherein the blocking element comprises a counter ramp that engages the ramp when the container holder is moved in relation to the shell form the first position to the second position.

* * * * *